United States Patent [19]

Pless et al.

[11] Patent Number: 5,131,388
[45] Date of Patent: Jul. 21, 1992

[54] IMPLANTABLE CARDIAC DEFIBRILLATOR WITH IMPROVED CAPACITORS

[75] Inventors: Benjamin D. Pless, Menlo Park, Calif.; William H. Elias, Six Mile, S.C.; Timothy A. Marguit, San Jose, Calif.

[73] Assignee: Ventritex, Inc., Sunnyvale, Calif.

[21] Appl. No.: 669,646

[22] Filed: Mar. 14, 1991

[51] Int. Cl.⁵ ............................................. A61N 1/39
[52] U.S. Cl. ................................................ 128/419 D
[58] Field of Search .................... 128/419 D; 361/323, 361/324, 502

[56] References Cited

U.S. PATENT DOCUMENTS 4,254,775  3/1981  Langer ........................... 128/419 D

OTHER PUBLICATIONS

"Implantable Cardioverters and Defibrillators" (Current Problems in Cardiology, vol. XIV, No. 12, Dec. 1989).

Primary Examiner—William E. Kamm
Assistant Examiner—Scott M. Getzow
Attorney, Agent, or Firm—Gerstman & Ellis, Ltd.

[57] ABSTRACT

An implantable cardiac defibrillator is provided having an energy source, a capacitor, and means coupled to the energy source for charging the capacitor. The capacitor comprises a planar layered structure of anode plates, cathode plates and means separating the anode plates and cathode plates. A polymeric envelope containing electrolyte encloses the layered structure. Electrical contact means extend from the anodes and cathodes to outside the envelope.

20 Claims, 2 Drawing Sheets

IMPLANTABLE CARDIAC DEFIBRILLATOR WITH IMPROVED CAPACITORS

FIELD OF THE INVENTION

The present invention concerns a novel implantable cardiac defibrillator, and more particularly, novel capacitors for use with an implantable cardiac defibrillator.

BACKGROUND OF THE INVENTION

Implantable defibrillators are implanted in patients suffering from potentially lethal arrhythmias. The device monitors cardiac activity and decides whether electrical therapy is required. If a tachycardia is detected, pacing or cardioversion therapy may be used to terminate the arrhythmia. If fibrillation is detected, defibrillation is the only effective therapy.

Both cardioversion and defibrillation require that a high voltage shock be delivered to the heart. Since it is impractical to maintain high voltage continuously ready for use, implantable defibrillators charge up energy storage capacitors prior to delivering a shock to the heart. Currently available defibrillators typically use tubular aluminum electrolytic capacitors as discussed in Troup, "Implantable Cardioverters and Defibrillators" (Current Problems in Cardiology, Volume XIV, Number 12, Dec. 1989, Year Book Medical Publishers, Chicago), and as disclosed in U.S. Pat. No. 4,254,775 entitled "Implantable Defibrillator and Package Therefor", issued in 1981.

Since the capacitors must store approximately 40 joules, their size is relatively large, and it is difficult to package them in a small implantable device. Currently available implantable defibrillators are relatively large (over 10 cubic inches), generally rectangular devices about an inch thick. The patient who has a device implanted may often be bothered by the presence of the large object in his or her abdomen. Furthermore, the generally rectangular shape can in some instances lead to skin erosion at the somewhat curved corners of the device. For the comfort of the patient we have found that it would be desirable to be able to make smaller, and more rounded implantable defibrillators. The size and configuration of the capacitors has been a major stumbling block in achieving this goal.

It is, therefore, an object of the present invention to provide efficient capacitor structure for an implantable cardiac defibrillator.

Another object of the present invention is to provide a capacitor structure which allows the construction of smaller, more physiologically-shaped implantable defibrillators.

Other objects of the present invention will become apparent as the description proceeds.

SUMMARY OF THE INVENTION

In accordance with the present invention, an implantable cardiac defibrillator is provided which comprises an energy source, a capacitor and means coupled to the energy source for charging the capacitor. The capacitor comprises a planar layered structured of anode plates, cathode plates and means separating the anode plates and cathode plates. A polymeric envelope containing electrolyte encloses the layered structure. First electric contact means extend from the anodes to outside the envelope and second electrical contact means extend from the cathodes to outside the envelope.

In the illustrative embodiment, the anodes are electrically connected in parallel and the cathodes are electrically connected in parallel. Each of the anodes comprises a double anode with an electrically conductive strip positioned between the plates forming the double anode.

In the illustrative embodiment, each of the anodes and cathodes comprises aluminum foil. The separating means are formed of paper and the electrically conductive strips comprise aluminum. The envelope comprises a solvent resistant polymeric material.

In the illustrative embodiment, a hermetic housing encloses the polymeric envelope. The first and second electrical contact means extend from the polymeric envelope to outside the hermetic housing.

In another embodiment, the defibrillator has a hermetic housing with a hermetic separator therein. The hermetic separator forms a first volume for containing the capacitor and a second volume, that is, segregated from the first volume, for containing other circuitry. The capacitor is located within the first volume and is hermetically segregated from the other circuitry whereby outgassing of the capacitor electrolyte does not affect the other circuitry.

Prior art implantable defibrillators use aluminum electrolytic "photo flash" capacitors packaged in tubular casings. The present invention also uses the aluminum electrolytic capacitor technology, but instead of winding the elements into a roll as in prior art devices, the inventive capacitor uses a stacked structure. This results in a generally flat capacitor which can be cut into arbitrary shapes to make more physiologically shaped implantable defibrillators. The use of a polymeric envelope to enclose the capacitor allows the assembly to be hermetically enclosed in a variety of materials, and allows a number of possibilities for the electrical termination of the component. An additional benefit results form the ability to incorporate the inventive capacitor directly into the implantable defibrillator structure to minimize the size of the device.

A more detailed explanation of the invention is provided in the following description and claims, and is illustrated in the accompanying drawings.

DETAILED DESCRIPTION OF THE ILLUSTRATIVE EMBODIMENTS

Figure 1:
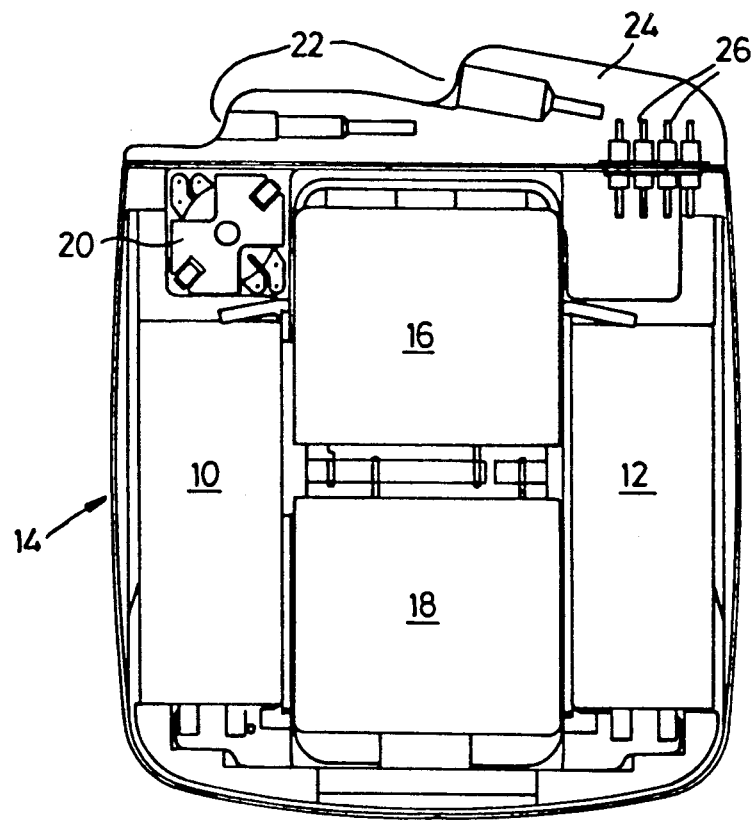
FIG. 1 is an elevational view of a prior art implantable defibrillator with the front of the housing removed for clarity.

In conventional implantable defibrillators the rectilinear profile of all the main components results in a defibrillator as shown in FIG. 1. In this example, the defibrillator capacitors 10 and 12 are situated near the hermetic titanium can 14. The two batteries 16 and 18 are stacked with the electronic circuitry (obscured by the batteries) in the center, and define the thickness of the device. The transformer 20, used to charge the capacitors 10, 12, is about the same thickness as the capacitors 10, 12. Ports 22 for the defibrillation and sensing leads are cast into an epoxy top 24, and hermetic feedthroughs 26 connect them to the defibrillator circuitry. Note that FIG. 1 has many construction details removed for clarity, and is only intended to show the size and positioning of the main components of the defibrillator.

Figure 2:
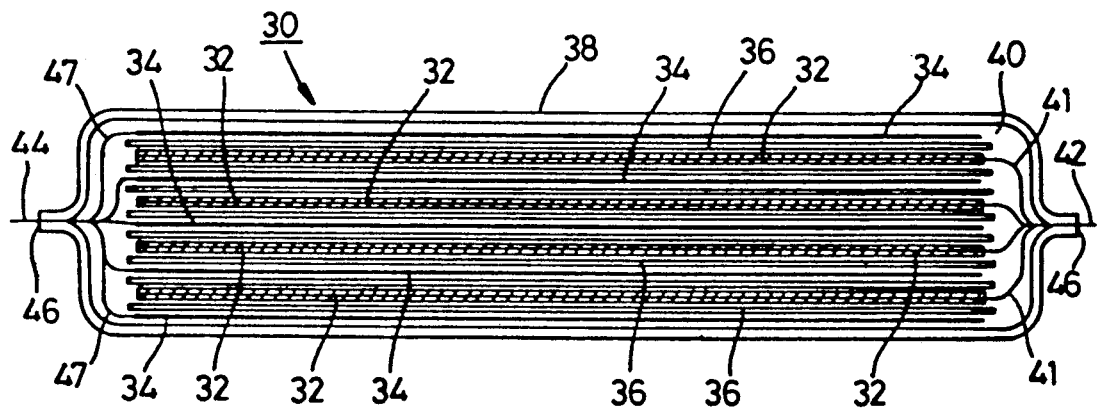
FIG. 2 is a diagrammatic cross-sectional elevation of a capacitor constructed in accordance with the present invention.

Referring to FIG. 2, a capacitor 30 is constructed in accordance with the present invention. The capacitor 30 is formed by a planar layered structure of double anode plates 32, cathode plates 34, and paper separators 36. The entire structure is sealed in a polymeric envelope or enclosure 38. The envelope is filled with electrolyte 40 suitable for an aluminum electrolytic capacitor, such as an electrolyte based on the solvent ethylene glycol. The anode plates are all electrically connected in parallel and brought out to form an electrical connection 42. Similarly the cathode plates are electrically connected in parallel and brought out to form an electrical connection 44. Where the electrical connections pass through the polymeric envelope 46 they are sealed against fluid leakage by adhesive bonding, heat sealing or molding.

The anode plates, cathode plates, and paper separators are made from materials typically used in high quality aluminum electrolytic capacitors. The individual anode plates 32 are comparatively stiff, high purity aluminum foil approximately 0.004 inches thick, processed by etching and forming to achieve a very high capacitance per unit area. The present state of the art for anode plates formed to operate at 385 volts is over six microfarads per square inch. The cathode plates 34 are high purity aluminum foil about 0.001 inches thick, and are comparatively flexible. The paper separators 36 are about 0.003 inches thick, and are made slightly larger than the cathode plates 34, and the double anodes 32, to assure that there is a physical barrier between the anodes and the cathodes of the finished capacitor.

The double anode 32 is formed by welding two anode plates together with an aluminum strip 41 between them for electrical contact. These aluminum strips 41 are welded together to make the electrical connection 42. Aluminum strips 47 are welded to each cathode 34 for electrical contact. These aluminum strips 47 are welded together to make the electrical connection 44. In the preferred embodiment, a silicon adhesive seals the polymeric envelope 38 at the seam 46. Nylon, Mylar ®, Polypropylene, Kapton ® and a number of other solvent resistant polymers with a thickness of about 0.005 inches are suitable for use as the polymeric envelope 38.

Once the capacitor 30 is constructed, it must undergo an ageing process as is required for any aluminum electrolytic capacitor. Ageing is accomplished by applying a voltage across the capacitor terminals and gradually raising the voltage from zero to the operating voltage of the capacitor. Once the working voltage is reached it is held until the leakage current stabilizes at an acceptably low value.

An illustrative example of a 300 microfarad, 350 volt capacitor has the following construction details:
Number of double anodes 32: 13
Number of cathodes 34: 14
Number of paper separators 36: 14
Area of cathode/anode: 3.25 square inches
Approximate thickness: 0.150 inches
Leakage current at 750 volts: 300 microamps The main advantage of this capacitor construction is the arbitrary shape of the anode and cathode plates. While the number and area of the plates is fixed for a given design, the shape can be modified to optimize packaging efficiency.

Another significant advantage of this structure is that it can be hermetically sealed more easily than conventional aluminum electrolytic capacitors. Conventional aluminum electrolytic capacitors do not use a polymeric envelope and so must be packaged in an aluminum case to avoid galvanic corrosion. The feedthroughs are sealed with rubber gaskets to contain the electrolyte. Unfortunately a rubber seal is not hermetic, and welding a hermetic feedthrough to the aluminum package is not possible. The result is that conventional aluminum electrolytic capacitors slowly outgas electrolyte vapors, which degrades the capacitor's performance, and can reduce the reliability of the implantable defibrillator's electronics. While it is possible to package a complete tubular aluminum electrolytic capacitor in a hermetic enclosure, the added material substantially increases the size and weight of the component.

Figure 3:
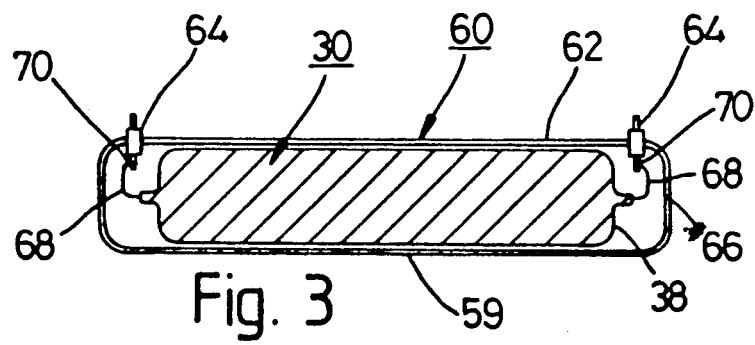
FIG. 3 is a cross-sectional view of a capacitor constructed in accordance with the principles of the present invention.

FIG. 3 shows the simple structure of the inventive capacitor 30 with a hermetic housing 60. Unlike conventional aluminum electrolytic capacitors, the housing 60 need not be of aluminum because of the polymeric envelope 38 used in the inventive capacitor. The capacitor 30 with its polymeric envelope 38 is placed in the bottom 59 of the housing 60. A top 62, with feedthroughs 64 for electrical connections, is welded along a seam 66 to make the enclosure hermetic. The aluminum terminals 68 of the capacitor are crimped or welded at point 70 to the feedthroughs 64.

The housing 60 is preferably made of stainless steel or titanium to provide good corrosion resistance for the life of the component. Laser or electron beam welding is preferred as the technique for joining the two halves 59, 62 of the hermetic enclosure 60. In some cases a deep drawn can with a lid may be preferable to the one shown, although it depends on the specific application of the component.

Figure 4:
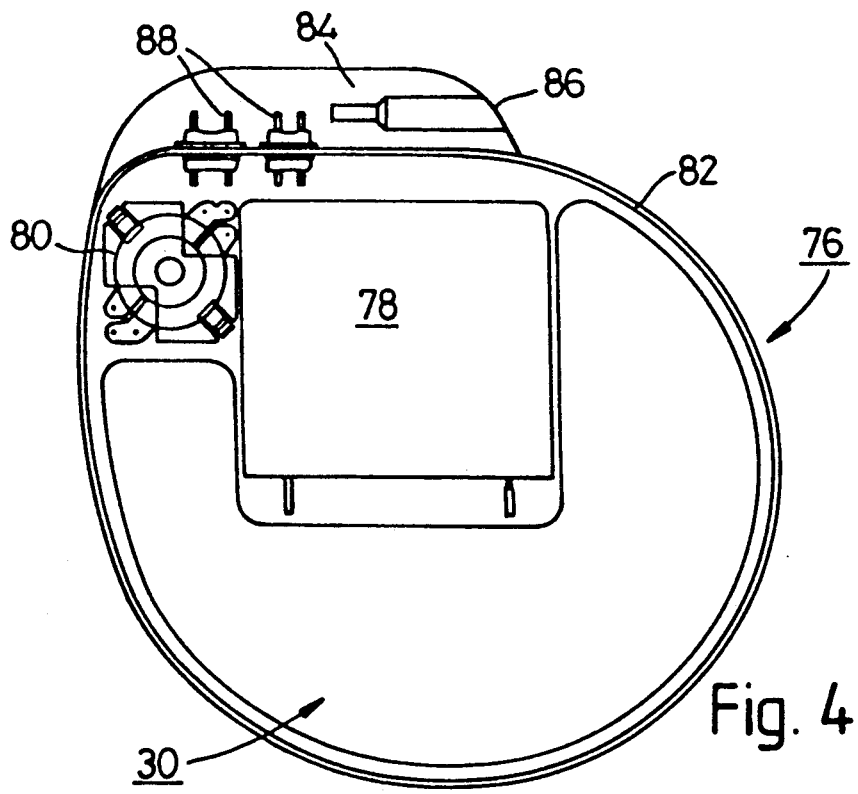
FIG. 4 is an elevational view of a cardiac defibrillator constructed in accordance with the principles of the present invention, with the front of the housing removed for clarity.

The improvement in packaging efficiency resulting from the use of the inventive capacitor can be seen in FIG. 4 which shows the flat capacitor 30 designed into an implantable defibrillator 76. The two batteries 78 are stacked (so one is obscured), and define the thickness of the device. The power transformer 80 (used to charge the defibrillator capacitors 30), and the batteries 78 are situated near the top of the defibrillator 76. Since the planar shape of the inventive capacitor 30 can be an arbitrarily design (so long as the 3.25 inch surface area requirement is met), it is used to surround the rectilinear components and provide a physiological shape. In this embodiment almost the entire outline is defined by the planar shape of the inventive capacitors, but a similar benefit may be derived by having a smaller portion of the device so defined. The electronic circuit is stacked with the two capacitors (so one capacitor and the electronic circuit is obscured by the visible capacitor 30 in FIG. 4), and is of the same general planar shape as the capacitors.

The capacitors and the rest of the circuitry are housed in a titanium enclosure 82 and an epoxy top 84 is cast in place to provide ports 86 for the sensing and defibrillating leads. Hermetic feedthroughs 88 are used to connect the lead ports 86 to the circuitry in the defibrillator in a conventional fashion. Note that FIG. 4 has many construction details removed for clarity, and is only intended to show the size and positioning of the main components of the defibrillator.

Figure 5:
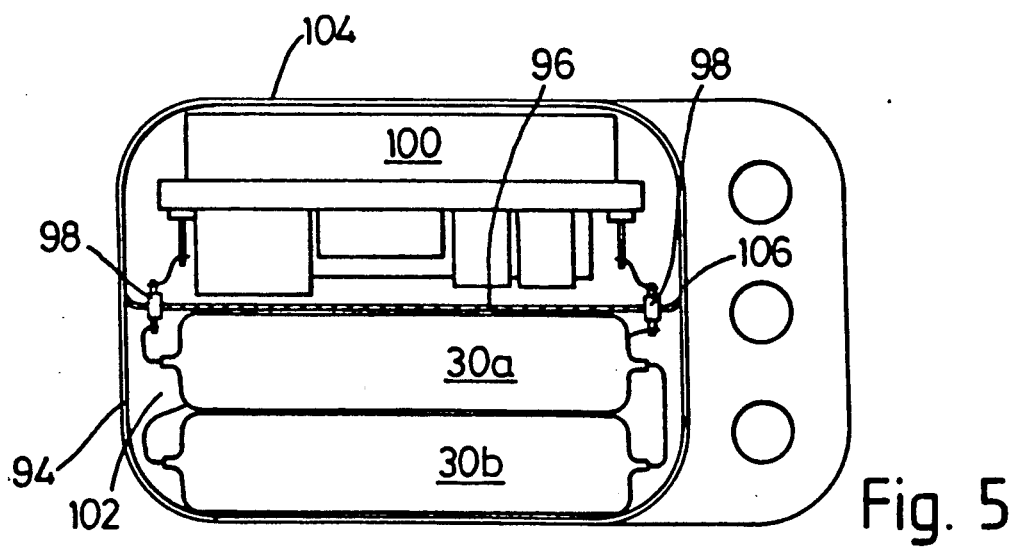
FIG. 5 is a cross-sectional view of a modified form of cardiac defibrillator constructed in accordance with the principles of the present invention.

While the capacitors 30 may be separately enclosed as shown in FIG. 3, they can also both be built into one hermetic enclosure, or they can even be built into the titanium (or stainless steel) defibrillator housing 94 as shown in FIG. 5. The ability to do this is a direct result of the novel structure of the capacitor. The capacitors 30a and 30b are put in a "false bottom" of the titanium housing 94 and welded closed with a lid 96. Feedthroughs 98 allow the capacitors to be connected to the circuity 100. The part 102 of the housing containing the capacitors is mated with the top housing 104 and is welded at 106 to provide a hermetic enclosure against infiltration of body fluids.

With this construction many benefits are obtained. The capacitors are in a separate hermetic enclosure so any outgassing of electrolyte does not affect the reliability of the other circuits. The additional material needed to enclose the capacitors is minimized since the defibrillator hermetic enclosure and the capacitor hermetic enclosure share a wall resulting in reduced thickness and weight. The planar nature of the inventive capacitor allows for high packaging efficiency while achieving an implantable defibrillator with a physiologic shape.

Although illustrative embodiments of the invention have been shown and described, it is to be understood that various modifications and substitutions may be made without departing from the spirit and scope of the present invention.

What is claimed is:

1. An implantable cardiac defibrillator which comprises:
   an energy source;
   a capacitor;
   means coupled to said energy source for charging said capacitor;
   said capacitor comprising a planar layered structure of anode plates, cathode plates and means separating the anode plates and cathode plates, an envelope containing electrolyte and enclosing said layered structure, first electric contact means extending from said anodes to outside said envelope, and second electrical contact means extending from said cathodes to outside said envelope.

2. An implantable defibrillator as defined by claim 1, in which said anodes are electrically connected in parallel and said cathodes are electrically connected in parallel.

3. An implantable defibrillator as described in claim 1 in which each of said anodes comprises a double anode with an electrically conductive strip positioned between the plates forming said double anode.

4. An implantable defibrillator as defined by claim 3, in which said electrically conductive strips comprise aluminum.

5. An implantable defibrillator as defined by claim 1, in which said anodes comprise aluminum foil.

6. An implantable defibrillator as defined by claim 1, in which said cathodes comprise aluminum foil.

7. An implantable defibrillator as defined by claim 1, in which said separating means are formed of paper.

8. An implantable defibrillator as defined by claim 1, in which said envelope comprises a solvent resistant polymeric material.

9. An implantable defibrillator as defined by claim 8, including a hermetic housing enclosing the polymeric envelope, said first and second electrical contact means extending from said polymeric envelope to outside of said hermetic housing.

10. An implantable defibrillator as defined by claim 8, said defibrillator having an external hermetic housing enclosing said polymeric envelope without requiring an intermediate metal casing enclosing the polymeric envelope.

11. An implantable defibrillator as defined by claim 1, in which said defibrillator has a hermetic housing with a hermetic separator therein, said hermetic separator forming a first volume for containing said capacitor and a second volume, segregated from the first volume, for containing other circuitry, said capacitor being located within said first housing and being hermetically segregated from the other circuitry whereby outgassing of the capacitor electrolyte does not affect the other circuitry.

12. An implantable defibrillator as defined by claim 1, said defibrillator having a housing with generally planar opposed sides, said capacitor substantially conforming in configuration to said generally planar opposed sides.

13. An implantable cardiac defibrillator which comprises:
   an energy source;
   a capacitor;
   means coupled to said energy source for charging said capacitor;
   said capacitor comprising a planar layered structure of anode plates, cathode plates and means separating the anode plates and cathode plates, said anode plates being electrically connected in parallel, said cathode plates being electrically connected in parallel, each of said anodes comprising a double anode with an electrically conductive strip positioned between the plates forming said double anode, a solvent resistant polymeric envelope containing electrolyte and enclosing said layered structure, first electric contact means extending from said anodes to outside said envelope, and second electrical contact means extending from said cathodes to outside said envelope.

14. An implantable defibrillator as defined by claim 13, including a hermetic housing enclosing the polymeric envelope, said first and second electrical contact means extending from said polymeric envelope to outside of said hermetic housing.

15. An implantable defibrillator as defined by claim 13, in which said defibrillator has a hermetic housing with a hermetic separator therein, said hermetic separator forming a first volume for containing said capacitor and a second volume, segregated from the first volume, for containing other circuitry, said capacitor being located within said first housing and being hermetically segregated from the other circuitry whereby outgassing of the capacitor electrolyte does not affect the other circuitry.

16. An implantable cardiac defibrillator which comprises:
   a generally planar housing;
   an energy source located within said housing;
   a capacitor located within said housing;

means coupled to said energy source for charging said capacitor, said charging means being located within said housing;

said capacitor comprising a planar layered structure of anode plates, cathode plates and means separating the anode plates and cathode plates, an envelope containing electrolyte and enclosing said layered structure, first electric contact means extending from said anodes to outside said envelope, and second electrical contact means extending from said cathodes to outside said envelope, said planar layered capacitor structure having a configuration that substantially conforms with the shape of the defibrillator housing.

17. An implantable defibrillator as defined by claim 16, in which said anodes are electrically connected in parallel and said cathodes are electrically connected in parallel.

18. An implantable defibrillator as defined by claim 16, in which of said anodes comprises a double anode with an electrically conductive strip positioned between the plates forming said double anode.

19. An implantable defibrillator as defined by claim 16, in which said defibrillator has a hermetic housing with a hermetic separator therein, said hermetic separator forming a first volume for containing said capacitor and a second volume, segregated from the first volume, for containing other circuitry, said capacitor being located within said first housing and being hermetically segregated from the other circuitry whereby outgassing of the capacitor electrolyte does not affect the other circuitry.

20. An implantable cardiac defibrillator which comprises:

a curvilinear housing;

an energy source located within said curvilinear housing;

A capacitor located within said curvilinear housing;

means coupled to said energy source for charging said capacitor, said charging means located within said curvilinear housing;

said capacitor comprising a planar layered structure of anode plates, cathode plates and means separating the anode plates and cathode plates, the outside dimension of said capacitor having a curvilinear shape generally conforming to the curvilinear shape of the defibrillator housing with said capacitor at least partially surrounding a portion of said energy source.

* * * * *